United States Patent
Toksöz et al.

(10) Patent No.: US 10,368,569 B2
(45) Date of Patent: Aug. 6, 2019

(54) NATURAL SWEETENER

(71) Applicant: MONTERO GIDA SANAYI VE TICARET A.S., Istanbul (TR)

(72) Inventors: Ahmet Toksöz, Istanbul (TR); Zafer Toksöz, Istanbul (TR); Onur Mutlu, Istanbul (TR); Ali Türkyilmaz, Istanbul (TR); Gülay Yelken, Istanbul (TR); Merve Zan, Istanbul (TR)

(73) Assignee: MONTERO GIDA SANAYI VE TICARET A.S., Istanbul (TR)

( * ) Notice: Subject to any disclaimer, the term of this patent is extended or adjusted under 35 U.S.C. 154(b) by 0 days.

(21) Appl. No.: 15/546,540

(22) PCT Filed: Jan. 26, 2016

(86) PCT No.: PCT/EP2016/051521
§ 371 (c)(1),
(2) Date: Jul. 26, 2017

(87) PCT Pub. No.: WO2016/120244
PCT Pub. Date: Aug. 4, 2016

(65) Prior Publication Data
US 2018/0213832 A1     Aug. 2, 2018

(30) Foreign Application Priority Data

Jan. 27, 2015 (TR) .............. a 2015/00903
Mar. 24, 2015 (TR) .............. a 2015/03546
Mar. 31, 2015 (TR) .............. a 2015/03923

(51) Int. Cl.
| | | |
|---|---|---|
| A61K 36/00 | (2006.01) | |
| A23L 27/30 | (2016.01) | |
| A23L 2/60 | (2006.01) | |
| A23L 33/105 | (2016.01) | |
| A23P 10/28 | (2016.01) | |
| A23G 1/48 | (2006.01) | |
| A61K 9/00 | (2006.01) | |
| A61K 47/12 | (2006.01) | |
| A61K 47/14 | (2017.01) | |
| A61K 47/18 | (2017.01) | |
| A61K 47/46 | (2006.01) | |

(52) U.S. Cl.
CPC .............. *A23L 27/33* (2016.08); *A23G 1/48* (2013.01); *A23L 2/60* (2013.01); *A23L 27/36* (2016.08); *A23L 33/105* (2016.08); *A23P 10/28* (2016.08); *A61K 9/0053* (2013.01); *A61K 47/12* (2013.01); *A61K 47/14* (2013.01); *A61K 47/183* (2013.01); *A61K 47/46* (2013.01); *A23V 2002/00* (2013.01)

(58) Field of Classification Search
CPC .................................................... A61K 36/00
See application file for complete search history.

(56) References Cited

U.S. PATENT DOCUMENTS

| | | |
|---|---|---|
| 2004/0022913 A1† | 2/2004 | Watson |
| 2006/0003053 A1 | 1/2006 | Ekanayake |
| 2007/0116851 A1 | 5/2007 | Shi et al. |
| 2008/0226797 A1 | 9/2008 | Lee |
| 2009/0162529 A1 | 6/2009 | Shi |
| 2010/0022462 A1* | 1/2010 | Shi ............ A61K 31/7048 514/25 |
| 2010/0040757 A1* | 2/2010 | Chin ............ A23F 5/243 426/594 |
| 2013/0136839 A1† | 5/2013 | Putter |

FOREIGN PATENT DOCUMENTS

WO    94/18855    † 9/1994

OTHER PUBLICATIONS

Alexiou et al, Prebiotic inulin-type fructans: nutritional benefits beyond dietary fibre source. Nutrition bulletin (2008), vol. 33, No. 3, pp. 227-233 (Year: 2008).*
European Patent Office; International Search Report; PCT/EP2016/051521; dated Mar. 21, 2016.
Patent Cooperation Treaty—Third Party Observation; PCT/EP2016/051521; dated May 27, 2017.

* cited by examiner
† cited by third party

*Primary Examiner* — Qiuwen Mi
(74) *Attorney, Agent, or Firm* — Kilpatrick Townsend & Stockton LLP

(57) ABSTRACT

The present invention relates to a natural sweetening composition comprising Luo Han Guo concentrate in an amount of 0.1 to 95% by weight and use in beverage, food, pharmaceutical, oral, dietetic, veterinary or tobacco products thereof.

26 Claims, 1 Drawing Sheet

LHG concentrate + Inulin + Lactose + Erythritol

↓ Mixing

Adding hazelnut puree/paste

↓ Grinding

Homogenizing and grinding the mixture

↓

Additional additives

↓

Conching

↓

Settling

↓

Shaping or filling

NATURAL SWEETENER

FIELD OF INVENTION

The present invention relates to a natural sweetening composition comprising Luo Han Guo concentrate in an amount of 0.1 to 95% by weight and use in beverage, food, pharmaceutical, oral, dietetic, veterinary or tobacco products thereof.

BACKGROUND OF INVENTION

Luo Han Guo (luohanguo) refers to the fruit of *Siraitia grosvenori*, formerly called *Momordica grosvenori*, a member of the Curcubitaceae. The plant is cultivated for its fruit Luo Han Guo, whose extract is nearly 300 times sweeter than sugar and has been used in China as a natural low-calorie sweetener and in traditional Chinese medicine to treat diabetes and obesity. Luo Han Guo is popularly considered a longevity aid and is used to balance heat buildup caused by internal conditions, life-forces, or external heat. It is used as an expectorant and antitussive to treat lung congestion, cough, other respiratory ailments, and sore throat. It also is used for constipation and chronic enteritis. Luo Han Guo is a low-caloric, low-glycemic food used as a natural sweetener in beverages and food.

Luo Han Guo is collected as a round green fruit that turns brown upon drying. The sweet taste of Luo Han Guo comes primarily from mogrosides, a group of terpene glycosides, present at the level of about 1% of the fleshy part of the fruit. Both the fresh and dried fruits are extracted to yield a powder that is 80% or more mogrosides. The mogrosides have been numbered, 1-5, and the main component is called mogroside-5, previously known as esgoside. Other, similar compounds from Luo Han Guo have been labeled siamenoside and neomogroside. The mixed mogrosides are estimated to be about 300 times as sweet as sugar by weight, so that the 80% extracts are nearly 250 times sweeter than sugar; pure mogrosides 4 and 5 may be 400 times as sweet as sugar by weight.

A process for making a useful sweetener from Luo Han Guo was patented in 1995 by Procter and Gamble Company in U.S. Pat. No. 5,411,755. As described in the patent application, the fruit itself, though sweet, has too many additional flavors that would make it unsuitable for widespread use as a sweetener, so P&G developed a method for processing it to eliminate the undesired flavors. In the P&G process, the fresh fruit is picked before ripening and allowed to complete its ripening during storage so that processing begins with the just-ripe fruit. The peel and seeds are then removed, and the mashed fruit becomes the basis of a concentrated fruit juice or puree that can be used in food manufacturing. Further processing involves using solvents to remove volatile and off-flavor components. Numerous sugar substitutes derived from Luo Han Guo by similar processes that isolate the sweet compounds are now readily available for manufacturing and for kitchen use.

Recent work on Luo Han Guo includes investigation of the antioxidant activity of the mogrosides (Shi H, et al., Antioxidant property of fructus momordicae extract, 1996 Biochemistry and Molecular Biology International 1996; 40 (6): 1111-1121.) and their potential use as cancer prevention compounds (Konoshima T and Takasaki M, Cancer-chemopreventive effects of natural sweeteners and related compounds, Pure Applied Chemistry 2002; 74(7): 1309-1316.). This suggested effect is based on the understanding that antioxidants can produce significant reversal or suppression of the early stage of cancer development, which has been an area of particular interest for tea drinking (Katiyar SK and Mukhtar H, Tea antioxidants in cancer chemoprevention, Journal of Cellular Biochemistry, Supplement 1997; 27: 59-67.). Further, Luo Han Guo and its sweetening component are often mentioned in relation to diabetes and obesity, because it can substitute for caloric sugars normally consumed in the diet.

Due to these neutral properties the potential application for natural sweetener composition is diverse, so this high quality sweetener can be used to replace sucrose in virtually every single food. Although sucrose, provides the most desirable taste to consumers, it is caloric and unhealthy. Furthermore, the natural sweetener composition is process friendly with virtually the same sweetening power as traditional sugar. But to be able to claim that you are using "natural sweetener" instead of sucrose provides a consumer friendly image and a positive sales argument. The carbohydrate fructose found in the natural sweetener composition is generally recognised as diabetic sweeteners, as compared to sucrose they are sugar substitutes and metabolised independent of insulin.

It has been also known numerous natural sweeteners are non-caloric; however, they exhibit sweet tastes that have different temporal profiles, maximal responses, flavor profiles, mouthfeels, and/or adaptation behaviors than that of sugar. Because of these differences, in a food or beverage, causes an unbalanced temporal profile and/or flavor profile. In addition to the difference in temporal profile, natural sweeteners generally exhibit:

(i) lower maximal response than sugar,
(ii) tastes including bitter, metallic, cooling, astringent, licorice-like taste, etc.,
(iii) sweetness which diminishes on iterative tasting.

It is well known to those skilled in the art of food/beverage/pharmaceutical composition that the sweetener in a composition requires balancing of the flavor and other taste components. If the taste profile of natural sweeteners could be modified to impart specific desired taste characteristics to be more sugar-like, the type and variety of compositions that may be prepared with that sweetener would be expanded significantly. Accordingly, it would be desirable to selectively modify the taste characteristics of natural sweeteners.

Another important point for the food/beverage/pharmaceutical composition is processability. The natural sweetening composition must be easily handled, mixed with excipients even having a larger particle size and must be processed into beverage, food, pharmaceutical, oral, dietetic, veterinary or tobacco products without the known and expected problems such as segregation or de-mix during the process steps. It is usually related with the choice of the sweeteners and their amounts or ratios between them.

In this invention it is surprisingly found that, a specific amount of Luo Han Guo changes the taste balance of a food or beverage or pharmaceutical compositions. They are slower in onset and longer in duration than the sweet taste produced by sucrose.

BRIEF DESCRIPTION OF THE DRAWING

The FIGURE illustrates the process steps of this invention.

DESCRIPTION OF THE INVENTION

Health trends have promoted an increased use of natural sweeteners in consumer diets. Amongst the many possibilities available to product developers is the option to enrich foods with "healthy ingredients" or perhaps to exchange one or more ingredients of the recipe in order to optimise the nutritional profile. For instance foods, which do not include additives or sugar, are perceived by the consumer, as natural and healthy. Despite their immense popularity, sweeteners and particularly sucrose recently gained bad publicity because of health concerns. That's why fruit sweeteners are becoming more and more important as a natural alternative to sucrose as they contain the fruit's own sugar spectrum.

Of increasing nutritional and physiological importance to today's consumer is the glycemic index (GI) that is much lower for fructose compared to that of glucose. Using glucose as the standard base, with a GI of 100, fructose has only a GI of around 20. The GI measures the glycemic response (an indication of the rate at which the blood glucose level rises and how it is sustained over time) after ingestion of carbohydrate foods. The consumption of food with low GI, such as fruit and vegetables, results in a slow increase of the blood glucose level. Food with a high GI, such as sucrose and white bread, results in a quick response of blood glucose insulin levels and therefore should not only be avoided by diabetics, but also by the growing number of health conscious consumers as there is growing evidence that over long time, a diet based on high-carbohydrate low-glycemic foods is beneficial towards health by preventing chronic diseases such as diabetes, coronary heart disease and possibly cancer.

In present invention, the phrase "concentrate" includes any Luo Han Guo product that is solid comprising "extract", "concentrated extract", "dried fruit", "de-juiced fruit", "lyophilized", "spray dried", "crystallized" or mixtures thereof.

In present invention, the concentrates comprising fructose, aromas, flavorings, vitamins, minerals, nutrients, concentrated juices, pieces of pulp and other remnants or mixtures thereof.

The main object of the present invention is to obtain a natural sweetening composition comprising Luo Han Guo concentrate in an amount of 0.1 to 95% by weight which overcomes the above described problems in prior art and have additive advantages over them.

Another main object of this invention is to obtain a sweetener composition that has sweeter taste because of the synergy between Luo Han Guo concentrate and any other sweeteners. This invention relates to a natural sweetening composition comprising Luo Han Guo concentrate, the composition is exhibiting synergy, i. e. providing greater sweetness than would be expected from simple summation of the sweetness contributed by the component sweetening agents.

Another main object of the present invention is to obtain a sweetener composition that does not increase the glycemic index. This invention provides a sweetener composition, which does not raise the glycemic index and provides the advantage of production simplicity.

Another main object of the present invention is to obtain a sweetener composition that is natural and healthy. Also it would be desirable to improve the taste of ingestible compositions that include natural ingredients to promote their use and the resulting health benefits. In this invention, the natural sweetener Luo Han Guo concentrate do not carry any glycemic index potential. Thus, a product is obtained which can be used by those who are in diets or by the diabetics.

The natural sweetening composition comprising Luo Han Guo concentrate in an amount of 0.1 to 80% by weight, and preferably in an amount of 0.1 to 65% by weight and more preferably in an amount of 0.1 to 50% by weight.

The natural sweetening composition comprising the content of Luo Han Guo concentrate is between 0.01 grams to 15 grams.

According to the special amounts and ratios mentioned below, the invention's advantages are reasonable preparing process, high flowability, uniform dispersion of sweetening agent and low moisture absorption. Specifically, this invention of the natural sweetening composition has the advantage of minimal changes in the products' physical characteristics, such as density, flowability, etc.; namely, preventing the final composition from becoming sticky which often occurs when a sweetening agent is added into a composition rather, and retains more of the characteristic flowability and density of the bulked composition with is normally adversely affected by conventional sweetening agent.

In this present invention, the natural sweetening composition further comprising at least one other sweetener.

In an embodiment, said at least one other sweetener is selected from the group comprises lactose, inuline, apple concentrate, erythritol, coconut sugar, locust bean gum; rebaudioside A, rebaudioside B, rebaudioside C, rebaudioside D, rebaudioside E, rebaudioside F, dulcoside A, dulcoside B, rubusoside, isomogroside V, 11-oxomogroside, steviol glycosides, *stevia*, stevioside, mogroside IV, mogroside V, mogroside VI, siamenoside, monatin and its salts (monatin SS, RR, RS, SR), curculin, glycyrrhizin, glycyrrhizic acid and its salts, thaumatin, monellin, mabinlin, brazzein, hernandulein, phyllodulcin, glycyphyllin, phloridzim, trilobatin, baiyunoside, osladin, polypodoside A, pterocaryoside A, pterocaryoside B, mukurozioside, phlomisoside I, periandrin I, abrusoside A, cyclocarioside I; a sweetener which is extracted from the group comprising *Stevia rebaudiana, Glycyrrhiza glabra, Siraitia grosvenorii*; sucrose, liquid sucrose, glucose, liquid glucose, fructose, liquid fructose, dextrose, galactose, lactulose, lactose, cellobiose, kojibiose, nigerose, isomaltose, .beta.,.beta.-trehalose, .alpha.,.beta.-trehalose, tagatose, sophorose, laminaribiose, gentiobiose, turanose, maltose, maltulose, palatinose, gentiobiulose, mannobiose, melibiose, melibiulose, rhamnose, ribose, rutinose, rutinulose, trehalose, xylobiose, xylose, corn syrups, fructo-oligosaccharides; erythritol, glycol, glycerol, threitol, arabitol, xylitol, ribitol, mannitol, sorbitol, dulcitol, iditol, isomalt, maltitol, lactitol, polyglycitol; apple skin extract (applephenon) or mixtures thereof.

Another embodiment of the invention, the natural sweetening composition further comprising a monosaccharide, a disaccharide, a polysaccharide, sugar alcohol or combinations thereof.

Monosaccharides comprise but not limited to glucose, fructose, galactose, xylose, ribose, or combinations thereof.

Disaccharides comprise but not limited to sucrose, lactulose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, xylobiose or combinations thereof. And it is preferably lactose.

Lactose is a disaccharide sugar derived from galactose and glucose that is found in milk. Lactose makes up around 2-8% of milk (by weight), although the amount varies among species and individuals, and milk with a reduced amount of lactose also exists. It is extracted from sweet or sour whey.

Polysaccharides comprise but not limited to fructooligosaccharide (FOS) and other fibers, maltooligosaccharides or combinations thereof.

Inulins are a group of naturally occurring polysaccharides produced by many types of plants, industrially most often extracted from chicory. The inulins belong to a class of dietary fibers known as fructans. Inulin is increasingly used in processed foods because it has unusually adaptable characteristics. Its flavour ranges from bland to subtly sweet (approx. 10% sweetness of sugar/sucrose). It can be used to replace sugar, fat and flour. This is advantageous because inulin contains 25-35% of the food energy of carbohydrates (starch, sugar). In addition to being a versatile ingredient, inulin has many health benefits. Inulin increases calcium absorption and possibly magnesium absorption, while promoting the growth of beneficial intestinal bacteria. In terms of nutrition, it is considered a form of soluble fiber and is sometimes categorized as a prebiotic. Due to the body's limited ability to process fructans, inulin has minimal increasing impact on blood sugar. It is considered suitable for diabetics and potentially helpful in managing blood sugar-related illnesses.

Sugar alcohols are food grade alcohols derived from one or more sugar molecules. Sugar alcohols include, for example, erythritol, glycol, glycerol, threitol, arabitol, xylitol, ribitol, mannitol, sorbitol, dulcitol, iditol, isomalt, maltitol, lactitol, polyglycitol and combinations thereof. And it is preferably erythritol.

Erythritol is especially useful as it can mitigate some of the bitter taste.

In one embodiment, the natural sweetening composition comprising at least one other sweetener and wherein the sweetener is lactose.

In one embodiment, the natural sweetening composition comprising Luo Han Guo concentrate and lactose.

In one embodiment, the natural sweetening composition comprising lactose in an amount of 1 to 99% by weight, and preferably in an amount of 1 to 97% by weight and more preferably in an amount of 1 to 95% by weight.

In an embodiment of the invention, the natural sweetening composition comprising Luo Han Guo concentrate and lactose wherein the ratios by weight of Luo Han Guo concentrate to lactose are between 0.01 to 95.00 and preferably 0.01:1, 0.1:1, 1:1, 1:2, 1:3, 1:4, 1:5, 1:6, 1:7, 1:8, 6:1, 50:1, 65:1, 80:1, 95:1; 0.1:93, 6:93, 50:93, 65:93, 80:93, 95:93; 0.1:95, 6:95, 50:95, 65:95, 80:95; 0.1:97, 6:97, 50:97, 65:97, 80:97, 95:97; 0.1:99, 6:99, 50:99, 65:99, 80:99, 95:99.

In one embodiment, the natural sweetening composition comprising at least one other sweetener and wherein the sweetener is inuline.

In one embodiment, the natural sweetening composition comprising Luo Han Guo concentrate and inuline.

In one embodiment, the natural sweetening composition comprising inuline in an amount of 0.1 to 80% by weight, and preferably in an amount of 0.1 to 65% by weight and more preferably in an amount of 0.1 to 50% by weight.

In an embodiment of the invention, the natural sweetening composition comprising Luo Han Guo concentrate and inuline wherein the ratios by weight of Luo Han Guo concentrate to inuline are between 0.01 to 95.00 and preferably 6:0.1, 50:0.1, 65:0.1, 80:0.1, 95:0.1; 0.1:1, 1:1, 2:1, 3:1, 4:1, 5:1, 6:1, 50:1, 65:1, 80:1, 95:1; 0.1:50, 6:50, 65:50, 80:50, 95:50.

In one embodiment, the natural sweetening composition comprising at least one other sweetener and wherein the sweetener is coconut sugar.

In one embodiment, the natural sweetening composition comprising Luo Han Guo concentrate and coconut sugar.

In one embodiment, the natural sweetening composition comprising at least one other sweetener and wherein the sweeteners are lactose and inuline.

In one embodiment, the natural sweetening composition comprising Luo Han Guo concentrate, lactose and inuline.

In one embodiment, the natural sweetening composition comprising Luo Han Guo concentrate in an amount of 0.1 to 80% by weight, and preferably in an amount of 0.1 to 65% by weight and more preferably in an amount of 0.1 to 50% by weight; lactose in an amount of 1 to 99% by weight, and preferably in an amount of 1 to 97% by weight and more preferably in an amount of 1 to 95% by weight; inuline in an amount of 0.1 to 80% by weight, and preferably in an amount of 0.1 to 65% by weight and more preferably in an amount of 0.1 to 50% by weight.

In a preferred embodiment, the natural sweetening composition comprising; Luo Han Guo concentrate in an amount of 0.1 to 50% by weight; lactose in an amount of 1 to 95% by weight; inuline in an amount of 0.1 to 50% by weight.

In one embodiment, the natural sweetening composition comprising at least one other sweetener and wherein the sweeteners are lactose, inuline and erythritol.

In one embodiment, the natural sweetening composition comprising Luo Han Guo concentrate, lactose, inuline and erythritol.

In one embodiment, the natural sweetening composition comprising at least one other sweetener and wherein the sweeteners are lactose, inuline and coconut sugar.

In one embodiment, the natural sweetening composition comprising Luo Han Guo concentrate, lactose, inuline and coconut sugar.

In one embodiment, the natural sweetening composition comprising at least one other sweetener and wherein the sweeteners are lactose, inuline and locust bean gum.

In one embodiment, the natural sweetening composition comprising Luo Han Guo concentrate, lactose, inuline and locust bean gum.

In one embodiment, the natural sweetening composition comprising at least one other sweetener and wherein the sweeteners are lactose, inuline, erythritol, coconut sugar and locust bean gum.

In one embodiment, the natural sweetening composition comprising Luo Han Guo concentrate, lactose, inuline, erythritol, coconut sugar and locust bean gum.

In one embodiment, the natural sweetening composition comprising at least one other sweetener and wherein the sweetener is apple concentrate.

In one embodiment, the natural sweetening composition comprising Luo Han Guo concentrate and apple concentrate.

In one embodiment, the natural sweetening composition comprising at least one other sweetener and wherein the sweeteners are lactose and apple concentrate.

In one embodiment, the natural sweetening composition comprising Luo Han Guo concentrate, lactose and apple concentrate.

In one embodiment, the natural sweetening composition comprising at least one other sweetener and wherein the sweeteners are inuline and apple concentrate.

In one embodiment, the natural sweetening composition comprising Luo Han Guo concentrate, inuline and apple concentrate.

In one embodiment, the natural sweetening composition comprising at least one other sweetener and wherein the sweeteners are lactose, inuline and apple concentrate.

In one embodiment, the natural sweetening composition comprising Luo Han Guo concentrate, lactose, inuline and apple concentrate.

In one embodiment, the natural sweetening composition comprising at least one other sweetener and wherein the sweeteners are lactose, inuline, erythritol and apple concentrate.

In one embodiment, the natural sweetening composition comprising Luo Han Guo concentrate, lactose, inuline, erythritol and apple concentrate.

In one embodiment, the natural sweetening composition comprising at least one other sweetener and wherein the sweeteners are lactose, inuline, coconut sugar and apple concentrate.

In one embodiment, the natural sweetening composition comprising Luo Han Guo concentrate, lactose, inuline, coconut sugar and apple concentrate.

In one embodiment, the natural sweetening composition comprising at least one other sweetener and wherein the sweeteners are lactose, inuline, locust bean gum and apple concentrate.

In one embodiment, the natural sweetening composition comprising Luo Han Guo concentrate, lactose, inuline, locust bean gum and apple concentrate.

In one embodiment, the natural sweetening composition comprising at least one other sweetener and wherein the sweeteners are lactose, inuline, erythritol, coconut sugar, locust bean gum and apple concentrate.

In one embodiment, the natural sweetening composition comprising Luo Han Guo concentrate, lactose, inuline, erythritol, coconut sugar, locust bean gum and apple concentrate.

In one embodiment, use of the natural sweetening composition comprising Luo Han Guo concentrate in an amount of 0.1 to 95% by weight in beverage, food, pharmaceutical, oral, dietetic, veterinary or tobacco products.

In one embodiment, use of the natural sweetening composition comprising Luo Han Guo concentrate, lactose and inuline in beverage, food, pharmaceutical, oral, dietetic, veterinary or tobacco products.

In a preferred embodiment, use of the natural sweetening composition comprising the sweeteners which are disclosed in this present invention in beverage, food, pharmaceutical, oral, dietetic, veterinary or tobacco products.

In this present invention, said products are solid, liquid or semisolid.

Use of the natural sweetening composition, wherein;
said beverages are selected from the group comprising colas, ginger ales, root beers, ciders, fruit-flavored soft drinks, powdered soft drinks or mixtures thereof; fruit juices originating in fruits or vegetables, fruit juices including squeezed juices or mixtures thereof, fruit juices containing fruit particles, fruit beverages, fruit juice beverages, beverages containing fruit juices, beverages with fruit flavorings, vegetable juices, juices containing vegetables, and mixed juices containing fruits and vegetables; drinks, sport drinks, energy drinks, near water or mixtures thereof; tea type or favorite type beverages which are coffee, cocoa, chocolate, black tea, green tea, oolong tea or mixtures thereof; beverages containing milk components which are milk beverages, coffee containing milk components, cafe au lait, milk tea, fruit milk beverages, drinkable yogurt, lactic acid bacteria beverages or mixtures thereof; dairy products; alcoholic beverages which are wine, beer, cider; distilled beverages which are spirit, liquor;

said food products are selected from the group comprising bakery products; desserts which are yogurt, jellies, drinkable jellies, puddings, Bavarian cream, blancmange, cakes, brownies, mousse or mixtures thereof; sweetened food products eaten at tea time or following meals; frozen foods; cold confections, types of ice cream which are ice cream, ice milk, lacto-ice or mixtures thereof; ice confections which are sherbets, dessert ices or mixtures thereof; ice cream; general confections, baked confections or steamed confections which are cakes, crackers, biscuits, buns with bean-jam filling or mixtures thereof; rice cakes and snacks; nut and peanut butter; table top products; general sugar confections which are chewing gum, hard candy, soft candy, mints, nougat candy, jelly beans or mixtures thereof; chocolates, chocolate creams; sauces including fruit flavored sauces, chocolate sauces or mixtures thereof; edible gels; cremes including butter cremes, flour pastes, whipped cream or mixtures thereof; jams including strawberry jam, marmalade or mixtures thereof; breads including sweet breads or other starch products or mixtures thereof; spice; general condiments including seasoned soy sauce used on roasted meats, roast fowl, barbecued meat or mixtures thereof, as well as tomato catsup, sauces, noodle broth or mixtures thereof; processed agricultural products, livestock products or seafood; processed meat products which are sausage or mixtures thereof; retort food products, pickles, preserves boiled in soy sauce, delicacies, side dishes; snacks which are potato chips, cookies or mixtures thereof; wafer, waffle, comets, bars, wafer sheet; cereal products, granola; baby food;

said pharmaceutical products are selected from the group comprising drugs or quasi-drugs that are administered orally or used in the oral cavity, wherein the drug may be in solid, liquid, gel or gas form which is a pill, tablet, spray, capsule, syrup, drop, troche agent, sachet, powder or mixtures thereof; herbal products, vitamins; nutraceutical products comprising any food or part of a food that may provide medicinal or health benefits, including the prevention and treatment of disease;

said oral products are selected from the group comprising hygienic or cosmetic products; personal care products which are oral compositions used in the oral cavity, mouth freshening agents, gargling agents, mouth rinsing agents, toothpaste, tooth polish, dentrifices, mouth sprays, teeth-whitening agents or mixtures thereof;

said dietetic products are selected from the group comprising dietary supplement;

said veterinary products are selected from the group comprising animal feed;

said tobacco products are selected from the group comprising smoke and smokeless tobacco products such as snuff, cigarette, pipe and cigar tobacco, and all forms of tobacco such as shredded filler, leaf, stem, stalk, homogenized leaf cured, reconstituted binders and reconstituted tobacco from tobacco dust, fines or ether sources in sheet, pellet or other forms, tobacco substitutes formulated from non-tobacco materials, dip or chewing tobacco.

In result, the art of sweetener products requires a novelty to provide the advantages of being healthy and natural, not increasing the glycemic index, production simplicity, cost-efficiency and sweeter taste because of the synergy between Luo Han Guo concentrate and any other sweeteners. In this case the sweetening composition can be easily handled, mixed with excipients even having a larger particle size and can be processed into beverage, food, pharmaceutical, oral, dietetic, veterinary or tobacco products without the known and expected problems such as segregation or de-mix during the process steps.

According to this invention, some examples are disclosed below:

Example 1: Sweetener Formulation

| Ingredients | Amount (% by weight) |
| --- | --- |
| LHG concentrate | 0.1-50 |
| Lactose | 1-95 |
| Inulin | 0.1-50 |

Production process of the formulation as following:

LHG concentrate, lactose and inulin are mixed. The resulting mixture is filled into sachets or added to the products as a sweetener.

Example 2: Sweetener Tablet Formulation

| Ingredients | Amount (% by weight) |
| --- | --- |
| LHG concentrate | 0.1-50 |
| Inulin | 0.1-50 |
| Lactose | 1-95 |
| Mannitol | 5-90 |
| Soy polysaccharide | 0.5-15 |
| Colloidal silicone dioxide | 0.1-5 |
| Hydrogenated vegetable oil | 1-10 |

Production process of the formulation as following:

LHG concentrate, inulin, lactose, mannitol, and soy polysaccharide are added to colloidal silicone dioxide and mixed. Hydrogenated vegetable oil is added to this first mixture and mixed them together in a short time. The resulting mixture is compressed in the form of tablets. The production preferably involves direct compressing method. It can alternatively be produced by wet granulation.

In this formulation, the sweetener is a natural sweetening composition of LHG concentrate and lactose and inulin, the mannitol used as a filler, and other excipients do not carry any glycemic index potential. Thus, a product is obtained which can be used by those who are in diets or by the diabetics.

Example 3: Chocolate Formulation

| Ingredients | Amount (% by weight) |
| --- | --- |
| LHG concentrate | 0.1-50 |
| Inulin | 0.1-50 |
| Lactose | 1-95 |
| Erythritol | 5-90 |
| Hazelnut or puree thereof | 10-30 |
| Cacao products | 1-45 |
| Milk products | 5-30 |
| Vegetable oil | 25-40 |
| *Vanilla* | 0.1-5 |

Production process of the formulation as following:

The mixture of LHG concentrate, inulin, lactose and erythritol is finely mixed and homogenized by means of a mixer. Then, a previously-grinded hazelnut puree is added to this mixture. The resulting mixture is grinded and mixed back so as to be homogenized.

To the preferably pre-ground mixture is added a liquid mixture composed of cacao powder, milk products, vanilla and vegetable oil. Then, conching and settling steps are applied to this mixture, where after the resultant mixture is prepared for sales, following a filling or shaping process as required by the form of the targeted product. The process steps may be illustrated by the FIGURE made part of this invention.

In result, thanks to the embodiment disclosed above, dietary chocolate composition comprising natural sweetening composition of LHG concentrate is obtained, with reduced calorie and low glycemic index.

Example 4: Oral Pharmaceutical Formulation

| Ingredients | Amount (% by weight) |
| --- | --- |
| Active ingredient | 1-95 |
| Anhydrous citric acid | 5-60 |
| LHG concentrate | 0.1-50 |
| Orange aroma | 0.1-5 |
| Disodium EDTA | 0.001-0.5 |
| Sodium stearyl fumarate | 0.1-10 |

Production process of the formulation as following:

Active ingredient, anhydrous citric, LHG concentrate, orange aroma, disodium EDTA and sodium stearyl fumarate are all sieved. All ingredients are mixed and homogenized. The resulting mixture is filled into sachets.

The invention claimed is:

1. A natural sweetening composition with synergistic sweeter taste comprising Luo Han Guo concentrate, lactose, and inulin; wherein the Luo Han Guo concentrate is present in an amount of 0.1 to 95% by weight.

2. The natural sweetening composition of claim 1, comprising Luo Han Guo concentrate in an amount of 0.1 to 80% by weight.

3. The natural sweetening composition claim 1, further comprising at least one other sweetener, wherein said at least one other sweetener is selected from the group consisting of apple concentrate, erythritol, coconut sugar, locust bean gum; rebaudioside A, rebaudioside B, rebaudioside C, rebaudioside D, rebaudioside E, rebaudioside F, dulcoside A, dulcoside B, rubusoside, isomogroside V, 11-oxomogroside, steviol glycosides, *stevia*, stevioside, mogroside IV, mogroside V, mogroside VI, siamenoside, monatin and monatin SS, RR, RS, SR, curculin, glycyrrhizin, glycyrrhizic acid and its salts, thaumatin, monellin, mabinlin, brazzein, hernandulein, phyllodulcin, glycyphyllin, phloridzim, trilobatin, baiyunoside, osladin, polypodoside A, pterocaryoside A, pterocaryoside B, mukurozioside, phlomisoside I, periandrin I, abrusoside A, cyclocarioside I; a sweetener which is extracted from the group consisting of *Stevia rebaudiana, Glycyrrhiza glabra, Siraitia grosvenorii*; sucrose, liquid sucrose, glucose, liquid glucose, fructose, liquid fructose, dextrose, galactose, lactulose, cellobiose, kojibiose, nigerose, isomaltose, .beta.,.beta.-trehalose, .alpha.,.beta.-trehalose, tagatose, sophorose, laminaribiose, gentiobiose, turanose, maltose, maltulose, palatinose, gentiobiulose, mannobiose, melibiose, melibiulose, rhamnose, ribose, rutinose, rutinulose, trehalose, xylobiose, xylose, corn syrups, fructo-oligosaccharides; glycol, glycerol, threitol, arabitol, xylitol, ribitol, mannitol, sorbitol, dulcitol, iditol, isomalt, maltitol, lactitol, polyglycitol; apple skin extract, applephenon or mixtures thereof.

4. The natural sweetening composition of claim 1, wherein lactose is present in an amount of 1 to 99% by weight.

5. The natural sweetening composition of claim 1, wherein inulin is present in an amount of 0.1 to 80% by weight.

6. The natural sweetening composition of claim 1, comprising Luo Han Guo concentrate in an amount of 0.1 to 65% by weight.

7. The natural sweetening composition of claim 1, comprising Luo Han Guo concentrate in an amount of 0.1 to 50% by weight.

8. The natural sweetening composition of claim 1, wherein lactose is present in an amount of 1 to 97% by weight.

9. The natural sweetening composition of claim 1, wherein lactose is present in an amount of 1 to 95% by weight.

10. The natural sweetening composition of claim 1, wherein inulin is present in an amount of 0.1 to 65% by weight.

11. The natural sweetening composition of claim 1, wherein inulin is present in an amount of 0.1 to 50% by weight.

12. The natural sweetening composition of claim 3, wherein the at least one other sweetener is erythritol.

13. The natural sweetening composition of claim 3, wherein the at least one other sweetener is coconut sugar.

14. The natural sweetening composition of claim 3, wherein the at least one other sweetener is locust bean gum.

15. The natural sweetening composition of claim 3, wherein the other sweeteners are erythritol, coconut sugar and locust bean gum.

16. The natural sweetening composition of claim 3, wherein the at least one other sweetener is apple concentrate.

17. The natural sweetening composition of claim 3, wherein the other sweeteners are erythritol and apple concentrate.

18. The natural sweetening composition of claim 3, wherein the other sweeteners are coconut sugar and apple concentrate.

19. The natural sweetening composition of claim 3, wherein the other sweeteners are locust bean gum and apple concentrate.

20. The natural sweetening composition of claim 3, wherein the other sweeteners are erythritol, coconut sugar, locust bean gum, and apple concentrate.

21. A beverage, food, pharmaceutical, oral, dietetic or veterinary product comprising a natural sweetening composition with synergistic sweeter taste comprising Luo Han Guo concentrate, lactose, and inulin; wherein the Luo Han Guo concentrate is present in an amount of 0.1 to 95% by weight of the natural sweetening composition.

22. The beverage, food, pharmaceutical, oral, dietetic or veterinary product of claim 21, wherein said product is solid, liquid or semisolid.

23. The beverage, food, pharmaceutical, oral, dietetic or veterinary product of claim 21, wherein:
said beverage product is selected from the group consisting of colas, ginger ales, root beers, ciders, fruit-flavored soft drinks, powdered soft drinks or mixtures thereof; fruit juices originating in fruits or vegetables, fruit juices including squeezed juices or mixtures thereof, fruit juices containing fruit particles, fruit beverages, fruit juice beverages, beverages containing fruit juices, beverages with fruit flavorings, vegetable juices, juices containing vegetables, and mixed juices containing fruits and vegetables; drinks, sport drinks, energy drinks, near water or mixtures thereof; tea type or favorite type beverages which are coffee, cocoa, chocolate, black tea, green tea, oolong tea or mixtures thereof; beverages containing milk components which are milk beverages, coffee containing milk components, cafe au lait, milk tea, fruit milk beverages, drinkable yogurt, lactic acid bacteria beverages or mixtures thereof; dairy products; alcoholic beverages which are wine, beer, cider; distilled beverages which are spirit, liquor;
said food product is selected from the group consisting of bakery products; desserts which are yogurt, jellies, drinkable jellies, puddings, Bavarian cream, blancmange, cakes, brownies, mousse or mixtures thereof; sweetened food products eaten at tea time or following meals; frozen foods; cold confections, types of ice cream which are ice cream, ice milk, lacto-ice or mixtures thereof; ice confections which are sherbets, dessert ices or mixtures thereof; ice cream; general confections, baked confections or steamed confections which are cakes, crackers, biscuits, buns with bean-jam filling or mixtures thereof; rice cakes and snacks; nut and peanut butter; table top products; general sugar confections which are chewing gum, hard candy, soft candy, mints, nougat candy, jelly beans or mixtures thereof; chocolates, chocolate creams; sauces including fruit flavored sauces, chocolate sauces or mixtures thereof; edible gels; cremes including butter cremes, flour pastes, whipped cream or mixtures thereof; jams including strawberry jam, marmalade or mixtures thereof; breads including sweet breads or other starch products or mixtures thereof; spice; general condiments including seasoned soy sauce used on roasted meats, roast fowl, barbecued meat or mixtures thereof, as well as tomato catsup, sauces, noodle broth or mixtures thereof; processed agricultural products, livestock products or seafood; processed meat products which are sausage or mixtures thereof; retort food products, pickles, preserves boiled in soy sauce, delicacies, side dishes; snacks which are potato chips, cookies or mixtures thereof; wafer, waffle, comets, bars, wafer sheet; cereal products, granola; baby food;
said pharmaceutical product is selected from the group consisting of drugs or quasi-drugs that are administered orally or used in the oral cavity, wherein the drug may be in solid, liquid, gel or gas form which is a pill, tablet, spray, capsule, syrup, drop, troche agent, sachet, powder or mixtures thereof; herbal products, vitamins; nutraceutical products comprising any food or part of a food that may provide medicinal or health benefits, including the prevention and treatment of disease;
said oral product is selected from the group comprising hygienic or cosmetic products; personal care products which are oral compositions used in the oral cavity, mouth freshening agents, gargling agents, mouth rinsing agents, toothpaste, tooth polish, dentrifices, mouth sprays, teeth-whitening agents or mixtures thereof;
said dietetic product is a dietary supplement; or
said veterinary product is an animal feed.

24. A method for making a beverage, food, pharmaceutical, oral, dietetic, or veterinary product, the method comprising admixing the components of a natural sweetening composition with synergistic sweeter taste; wherein the natural sweetening composition with synergistic sweeter taste comprises: Luo Han Guo concentrate, lactose, and inulin; and wherein the Luo Han Guo concentrate is present in an amount of 0.1 to 95% by weight of the natural sweetening composition.

25. The method of claim 24, wherein said product is solid, liquid, or semisolid.

26. The method of claim 24, wherein:

said beverage product is selected from the group consisting of colas, ginger ales, root beers, ciders, fruit-flavored soft drinks, powdered soft drinks or mixtures thereof; fruit juices originating in fruits or vegetables, fruit juices including squeezed juices or mixtures thereof, fruit juices containing fruit particles, fruit beverages, fruit juice beverages, beverages containing fruit juices, beverages with fruit flavorings, vegetable juices, juices containing vegetables, and mixed juices containing fruits and vegetables; drinks, sport drinks, energy drinks, near water or mixtures thereof; tea type or favorite type beverages which are coffee, cocoa, chocolate, black tea, green tea, oolong tea or mixtures thereof; beverages containing milk components which are milk beverages, coffee containing milk components, cafe au lait, milk tea, fruit milk beverages, drinkable yogurt, lactic acid bacteria beverages or mixtures thereof; dairy products; alcoholic beverages which are wine, beer, cider; distilled beverages which are spirit, liquor;

said food product is selected from the group consisting of bakery products; desserts which are yogurt, jellies, drinkable jellies, puddings, Bavarian cream, blancmange, cakes, brownies, mousse or mixtures thereof; sweetened food products eaten at tea time or following meals; frozen foods; cold confections, types of ice cream which are ice cream, ice milk, lacto-ice or mixtures thereof; ice confections which are sherbets, dessert ices or mixtures thereof; ice cream; general confections, baked confections or steamed confections which are cakes, crackers, biscuits, buns with bean-jam filling or mixtures thereof; rice cakes and snacks; nut and peanut butter; table top products; general sugar confections which are chewing gum, hard candy, soft candy, mints, nougat candy, jelly beans or mixtures thereof; chocolates, chocolate creams; sauces including fruit flavored sauces, chocolate sauces or mixtures thereof; edible gels; cremes including butter cremes, flour pastes, whipped cream or mixtures thereof; jams including strawberry jam, marmalade or mixtures thereof; breads including sweet breads or other starch products or mixtures thereof; spice; general condiments including seasoned soy sauce used on roasted meats, roast fowl, barbecued meat or mixtures thereof, as well as tomato catsup, sauces, noodle broth or mixtures thereof; processed agricultural products, livestock products or seafood; processed meat products which are sausage or mixtures thereof; retort food products, pickles, preserves boiled in soy sauce, delicacies, side dishes; snacks which are potato chips, cookies or mixtures thereof; wafer, waffle, comets, bars, wafer sheet; cereal products, granola; baby food;

said pharmaceutical product is selected from the group consisting of drugs or quasi-drugs that are administered orally or used in the oral cavity, wherein the drug may be in solid, liquid, gel or gas form which is a pill, tablet, spray, capsule, syrup, drop, troche agent, sachet, powder or mixtures thereof; herbal products, vitamins; nutraceutical products comprising any food or part of a food that may provide medicinal or health benefits, including the prevention and treatment of disease;

said oral product is selected from the group comprising hygienic or cosmetic products; personal care products which are oral compositions used in the oral cavity, mouth freshening agents, gargling agents, mouth rinsing agents, toothpaste, tooth polish, dentrifices, mouth sprays, teeth-whitening agents or mixtures thereof;

said dietetic product is a dietary supplement; or said veterinary product is an animal feed.

* * * * *